(12) United States Patent
Dimatteo et al.

(10) Patent No.: US 9,717,873 B2
(45) Date of Patent: Aug. 1, 2017

(54) ROTATING ELECTRICAL CONNECTOR ADN RESPIRATORY GAS DELIVERY SYSTEM EMPLOYING SAME

(75) Inventors: Mark William Dimatteo, Irwin, PA (US); Mark Barclay, Saxonburg, PA (US); Anthony Jon Bafile, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 14/118,632

(22) PCT Filed: May 15, 2012

(86) PCT No.: PCT/IB2012/052415
§ 371 (c)(1),
(2), (4) Date: Nov. 19, 2013

(87) PCT Pub. No.: WO2012/160477
PCT Pub. Date: Nov. 29, 2012

(65) Prior Publication Data
US 2015/0136127 A1    May 21, 2015

Related U.S. Application Data

(60) Provisional application No. 61/488,311, filed on May 20, 2011.

(51) Int. Cl.
*A61M 16/00* (2006.01)
*A61M 16/08* (2006.01)
(Continued)

(52) U.S. Cl.
CPC .... *A61M 16/0816* (2013.01); *A61M 16/0003* (2014.02); *A61M 16/0066* (2013.01);
(Continued)

(58) Field of Classification Search
None
See application file for complete search history.

(56) References Cited

U.S. PATENT DOCUMENTS 3,958,297 A * 5/1976 Hukuba ................ A47L 9/0063
15/315
4,550,957 A * 11/1985 Keane ................... A47L 9/2868
439/13
(Continued)

FOREIGN PATENT DOCUMENTS

CN         1691437 A      11/2005
CN       101106243 A       1/2008
(Continued)

OTHER PUBLICATIONS

M Series Tubing Swivel, Mar. 9, 2011 http://www.cpap-supply.com/M-Series-Tubing-Swivel-p/1029532.htm  http://www.cpap-supply.com/Articles.asp?ID=144.
(Continued)

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

A connection assembly for rotateably and electrically coupling an accessory to a main device includes a housing portion, a rotatable port assembly, and a wire assembly. An end of the port assembly is coupled to the accessory. The port assembly includes an electrical connector member having a first connector end electrically coupled to the accessory. The wire assembly has an electrical wire member having a first end electrically coupled to a second connector end of the electrical connector member and a second end electrically coupled to a power supply. The wire member is spooled around the port assembly and encased in a chamber defined between the housing portion and the port assembly. Rotation of the port assembly in opposite directions causes
(Continued)

the electrical wire member to spool more and less tightly around the port assembly without causing pinching or tangling of wires.

14 Claims, 8 Drawing Sheets

(51) Int. Cl.
  *A61M 16/10*  (2006.01)
  *A61M 16/16*  (2006.01)
  *H01R 35/04*  (2006.01)
  *A61M 39/10*  (2006.01)
  *A61M 16/04*  (2006.01)
  *A61M 16/06*  (2006.01)

(52) U.S. Cl.
  CPC ........ *A61M 16/0069* (2014.02); *A61M 16/04* (2013.01); *A61M 16/06* (2013.01); *A61M 16/0825* (2014.02); *A61M 16/10* (2013.01); *A61M 16/109* (2014.02); *A61M 16/1075* (2013.01); *A61M 16/1095* (2014.02); *A61M 16/16* (2013.01); *A61M 39/10* (2013.01); *A61M 39/1055* (2013.01); *H01R 35/04* (2013.01); *A61M 2016/003* (2013.01); *A61M 2016/0039* (2013.01); *A61M 2205/3368* (2013.01); *A61M 2205/502* (2013.01); *A61M 2205/52* (2013.01)

(56) References Cited

U.S. PATENT DOCUMENTS

| | | | |
|---|---|---|---|
| 5,148,802 A | | 9/1992 | Sanders |
| 5,165,398 A | | 11/1992 | Bird |
| 5,313,937 A | | 5/1994 | Zdrojkowski |
| 5,433,193 A | | 7/1995 | Sanders |
| 5,632,269 A | | 5/1997 | Zdrojkowski |
| 5,803,065 A | | 9/1998 | Zdrojkowski |
| 6,029,664 A | | 2/2000 | Zdrojkowski |
| 6,089,874 A | * | 7/2000 | Kroulik ............... H01R 35/025 439/11 |
| 6,494,396 B2 | * | 12/2002 | Sugata ................. B60R 16/027 242/388 |
| 6,539,940 B2 | | 4/2003 | Zdrojkowski |
| 6,626,175 B2 | | 9/2003 | Jafari |
| 7,052,281 B1 | * | 5/2006 | Meyberg ............... H02G 11/02 439/4 |
| 7,393,222 B2 | | 7/2008 | Asakura |
| 7,677,246 B2 | | 3/2010 | Kepler |
| 7,819,665 B1 | * | 10/2010 | Nishizawa ............ H01R 24/30 439/13 |
| 8,758,024 B2 | * | 6/2014 | Adachi .................. H01R 35/04 439/15 |
| 2002/0029805 A1 | | 3/2002 | Gallant |
| 2003/0116963 A1 | | 6/2003 | Teuscher |
| 2004/0100092 A1 | * | 5/2004 | Sranka .................... F16L 39/06 285/121.3 |
| 2008/0105257 A1 | | 5/2008 | Klasek |
| 2008/0190427 A1 | | 8/2008 | Payton |
| 2009/0023304 A1 | * | 1/2009 | Gerard ................. H01R 13/652 439/13 |
| 2009/0320840 A1 | | 12/2009 | Klasek |
| 2010/0316508 A1 | * | 12/2010 | Horng ................. F04D 25/0653 417/352 |
| 2013/0064700 A1 | * | 3/2013 | Wu ......................... F04D 17/16 417/423.7 |
| 2014/0158125 A1 | | 6/2014 | O'Donnell |

FOREIGN PATENT DOCUMENTS

| | | |
|---|---|---|
| EP | 1369141 A1 | 10/2003 |
| JP | 2218585 A | 8/1990 |
| JP | H03213293 A | 9/1991 |
| JP | 2001016753 A | 1/2001 |
| JP | 200160484 A | 3/2001 |
| JP | 2003500120 | 1/2003 |
| JP | 2003311673 A | 11/2003 |
| JP | 2005525145 | 8/2005 |
| JP | 2009519093 A | 5/2009 |
| JP | 2010508875 A | 3/2010 |
| WO | WO02079685 A1 | 10/2002 |
| WO | WO2005028012 A1 | 3/2005 |

OTHER PUBLICATIONS

BiPAP AVAPS C Series Noninvasive Ventilator with Heated Humidifier, Carrying Case and 6' Air Tubing, Mar. 9, 2011 http://www.cpapman.com/store/bipap-avaps-c-series-noninvasive-ventilator-with-heated-humidifier-carrying-case-and-6-air-tubing.html.

BiPAP Auto PR System One Series with Bi-Flex, Heated Humidifier, 6' Air Tubing and Carrying Case, Mar. 9, 2011 http://www.cpapman.com/store/bipap-auto-pr-system-one-series-with-bi-flex-heated-humidifier-6-air-tubing-and-carrying-case.html.

Senske A., "Wher's My Respironics REMstar M Series Hose Swivel", CPAP Machines and CPAP Masks—Where's My Respironics REMstar M Series Hose, Jul. 22, 2007 http://www.cpap-supply.com/Articles.asp?ID=144.

\* cited by examiner

ROTATING ELECTRICAL CONNECTOR ADN RESPIRATORY GAS DELIVERY SYSTEM EMPLOYING SAME

CROSS-REFERENCE TO RELATED APPLICATIONS

This patent application claims the priority benefit under 35 U.S.C. §371 of international patent application no. PCT/IB2012/052415, filed May 15, 2012, which claims the priority benefit under 35 U.S.C. §119(e) of U.S. Provisional Application No. 61/488,311 filed on May 20, 2011, the contents of which are herein incorporated by reference.

BACKGROUND OF THE INVENTION

1. Field of the Invention

The present invention relates to electrical component connectors, and, in particular, to a rotatable connection assembly that includes an outlet port that both provides power for an electrical accessory component and allows for rotation of the connected component. The connection assembly may be used in a device such as, without limitation, a gas delivery system for providing respiratory therapy (e.g., non-invasive ventilation and pressure support systems).

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Humidifiers are frequently provided between or integral with the gas flow generating portion of a respiratory therapy system and the user interface in order to humidify the otherwise relatively-dry compressed air that is generated. Within the humidifier, water is allowed to evaporate to produce vapor within a reservoir while breathing gas is passed over the surface of the water. Increased water vapor within the reservoir increases the capability to provide more humidity to the gas that is delivered to a user. This increase in gas stream humidity is typically accompanied by an increase in the gas stream temperature. When the ambient temperature around the respiratory therapy system is below the gas stream temperature, condensation can form on the inside of the patient breathing circuit.

It is presently known to heat the patient breathing circuit in order to reduce the formation of condensation on and/or within the patient breathing circuit. To increase mobility of the patient breathing circuit, a swivel port at the outlet of the humidifier is often used. The swivel port must provide power to the heating mechanism of the patient breathing circuit while mitigating wiring management issues by allowing rotation of the port without pinching or binding of the wires. Current swivel port solutions, however, require multiple parts and/or difficult and/or lengthy assembly processes.

SUMMARY OF THE INVENTION

Accordingly, it is an object of the present invention to provide an outlet port for a device such as a respiratory gas delivery system that overcomes the shortcomings of conventional outlet ports. This object is achieved according to one embodiment of the present invention by providing a simple and cost effective rotatable connection assembly that includes an outlet port that both provides power for a connected component, such as a heating tube, and allows for rotation of the connected component without pinching or tangling of wires.

In one embodiment, a connection assembly is provided for rotateably coupling an electrical accessory component, such as a heating gas delivery tube, to a main device, such as a respiratory gas delivery system (e.g., a CPAP machine or a non-invasive ventilation system), and providing electrical power from the main device to the accessory component. The connection assembly includes a housing portion (e.g., a pivoting lid forming a part of the main housing of the main device), a port assembly rotateably coupled to the housing portion, and a wire assembly. The port assembly has a first end and a second end, the second end of the port assembly being coupled to the accessory component, the port assembly including an electrical connector member having a first connector end electrically coupled to the accessory component and a second connector end. The wire assembly has an electrical wire member having a first end electrically coupled to the second connector end and a second end electrically coupled to a power supply of the main device. A portion of the electrical wire member is spooled around the first end of the port assembly and encased in a chamber defined between the housing portion and the port assembly, wherein rotation of the port assembly in a first direction causes the portion of the electrical wire member to spool more tightly around the first end of the port assembly and rotation of the port assembly in a second direction causes the portion of the electrical wire member to spool less tightly around the first end of the port assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
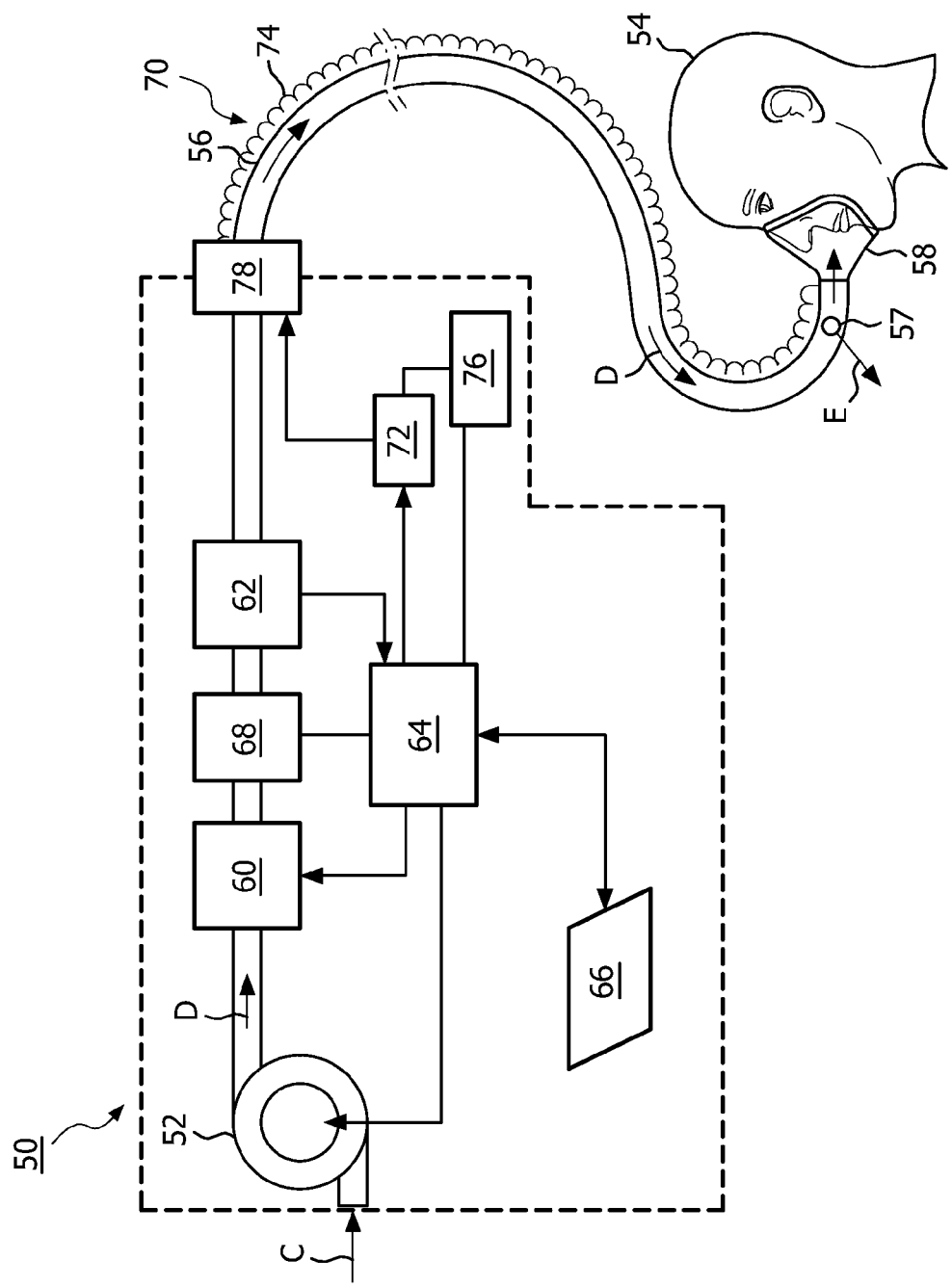
FIG. 1 is a schematic diagram of a pressure support system according to one particular, non-limiting embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of a pressure support system 50 according to one particular, non-limiting embodiment of the present invention. Referring to FIG. 1, pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure.

In the exemplary embodiment, gas flow generator 52 is capable of providing a flow of breathing gas ranging in pressure from 3-30 $cmH_2O$. The pressurized flow of breathing gas, generally indicated by arrow D from gas flow generator 52, is delivered via a delivery conduit 56 to a breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 shown in FIG. 1 is what is known as a single-limb system, meaning that the patient circuit includes only delivery conduit 56 connecting patient 54 to pressure support system 50. As such, an exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of a valve 60 provided in delivery conduit 56. Valve 60 controls the pressure of the flow of breathing gas from flow generator 52 that is delivered to patient 54. For present purposes, flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54.

If valve 60 is eliminated, the pressure generating system corresponds to flow generator 52 alone, and the pressure of gas in the patient circuit is controlled, for example, by controlling the motor speed of flow generator 52.

Pressure support system 50 further includes a flow sensor 62 that measures the flow rate of the breathing gas within delivery conduit 56. In the particular embodiment shown in FIG. 1, flow sensor 62 is interposed in line with delivery conduit 56, most preferably downstream of valve 60. Flow sensor 62 generates a flow signal, $Q_{measured}$, that is provided to a controller 64 and is used by controller 64 to determine the rate of flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such a leaks at the mask/patient interface. The present invention contemplates using any known or hereafter developed technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50. An input/output device 66 is provided for setting various parameters used by pressure support system 50, as well as for displaying and outputting information and data to a user, such as a clinician or caregiver.

In the illustrated embodiment, pressure support system 50 also includes a humidifier 68 provided in the main housing 69 of pressure support system 50. Alternatively, humidifier 68 may be separate from and located external to main housing 69. Humidifier 68 further improves comfort by providing moisture in the supplied gas. In the exemplary embodiment, humidifier 68 is a passover type humidifier. U.S. Patent Application Publication No. 2007/0169776, incorporated herein by reference in its entirety, discloses an exemplary humidifier device suitable for use in the present invention. Humidifier devices having alternative designs may also be used.

Pressure support system 50 further includes patient circuit heating apparatus 70, which in the illustrated embodiment comprises heating control unit 72 (provided in main housing 69) operatively coupled to a heating coil 74. Heating coil 74 is positioned adjacent to or within delivery conduit 56 of the patient circuit and is structured to heat the patient circuit under the control of heating control unit 72. Heating control unit 72 is operatively coupled to and controlled by controller 64. The patient circuit heating apparatus 70 including heating control unit 72 and heating coil 74 is but one example of a suitable heating apparatus, and it will be understood that other heating apparatuses may be employed in the present invention. Pressure support system 50 further includes a suitable power supply 76 for supplying power to the components of pressure support system 50 that need it. Delivery conduit 56 and heating coil 74 are physically and electrically connected to main housing 69 through a connection assembly 78 of the present invention that is described in greater detail below.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
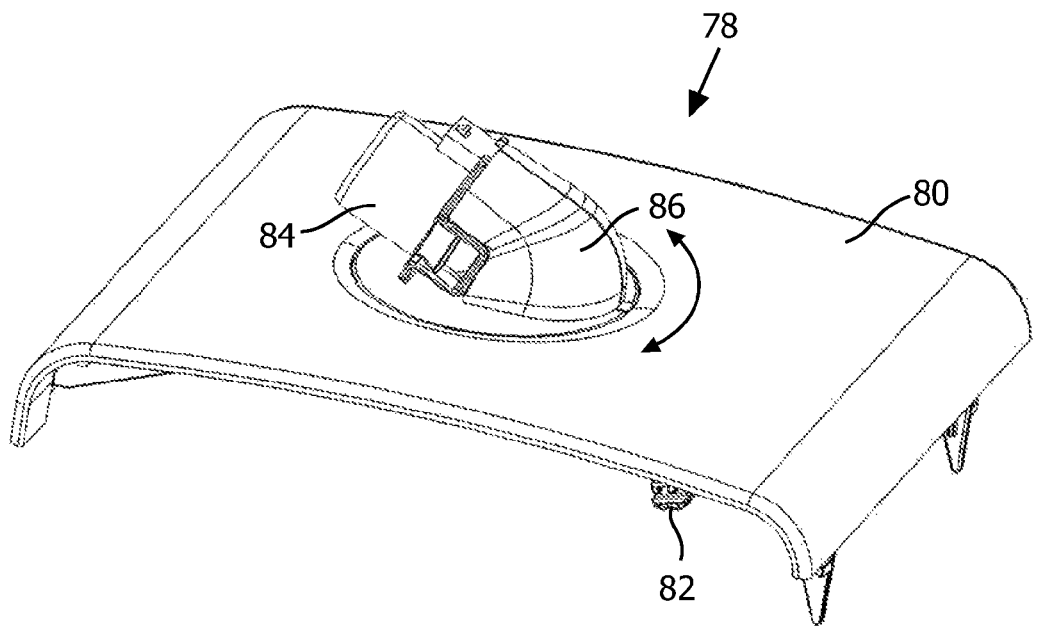
FIGS. 2 and 3 are top and bottom isometric views, respectively, of a connection assembly forming a part of the pressure support system of FIG. 1 according to the exemplary embodiment of the present invention.
Figure 3:
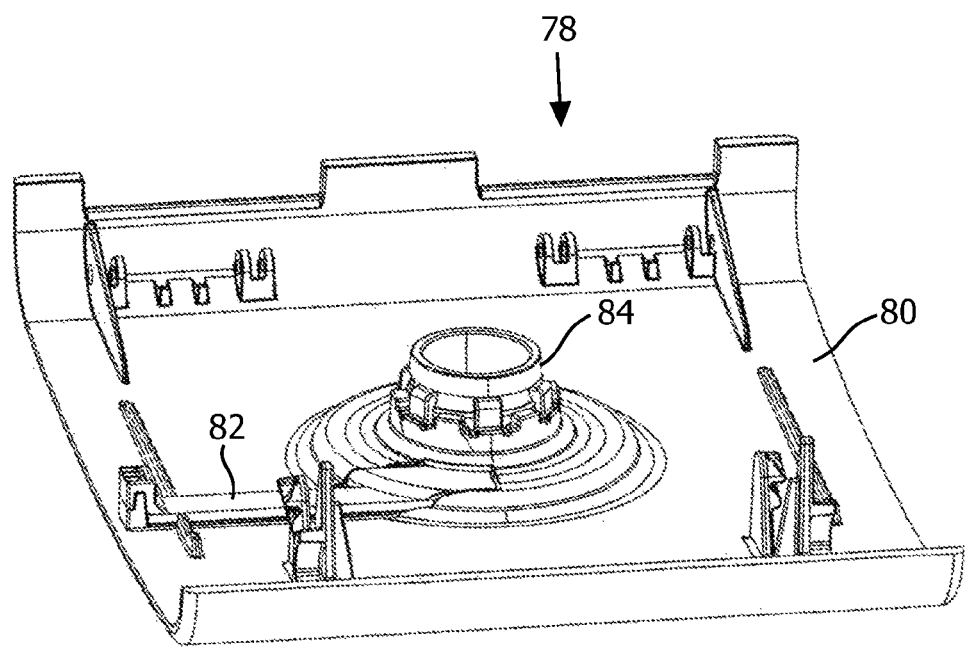

FIGS. 2 and 3 are top and bottom isometric views, respectively, of connection assembly 78 according to the exemplary embodiment of the present invention. Connection assembly 78 includes the following four main components: (i) a housing lid member 80, (ii) a wire assembly 82, (iii) a swivel connector member 84, and (iv) a swivel cover assembly 86. Each of those four components will first be described in detail below, followed by a discussion of the assembly and operation of connection assembly 78.

Figure 4:
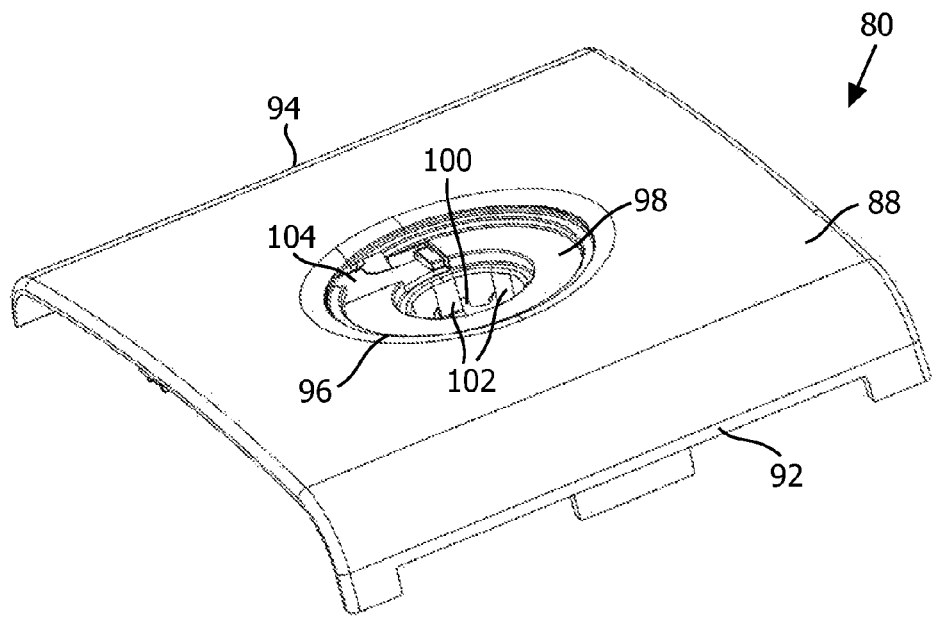
FIGS. 4 and 5 are top and bottom isometric views, respectively, of a housing lid member forming a part of the connection assembly of FIGS. 2 and 3.
Figure 5:
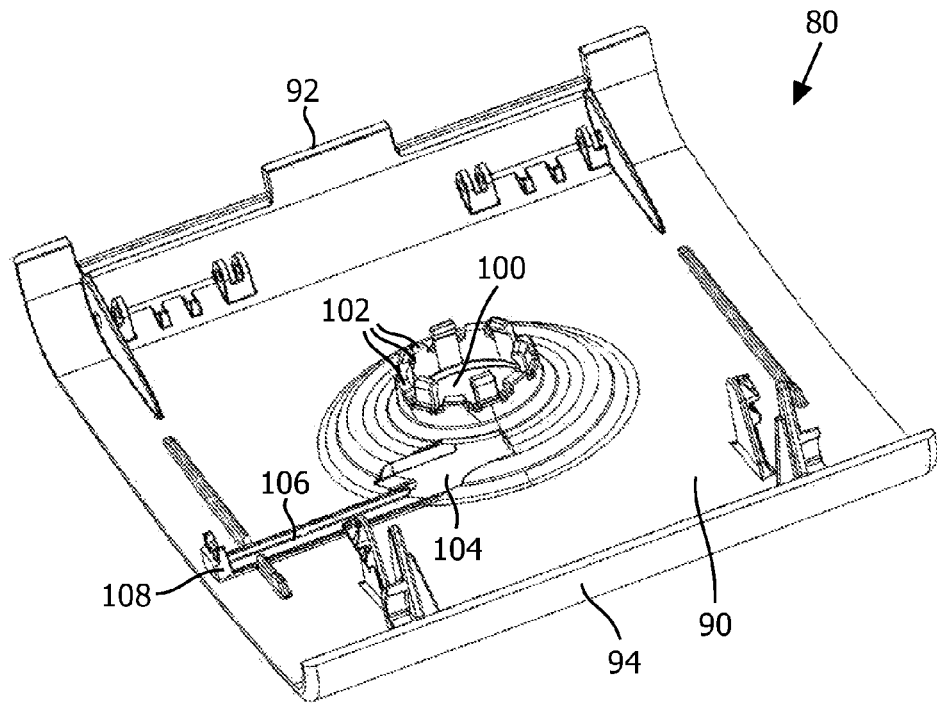

FIGS. 4 and 5 are top and bottom isometric views, respectively, of housing lid member 80. Housing lid member 80 includes a top surface 88, a bottom surface 90, a first side 92 and a second side 94. In the illustrated embodiment, housing lid member 80 is structured to be coupled to main housing 69 (to form a part thereof) in a manner that allows housing lid member 80 to be pivoted about first side 92 (by way of a plurality of pins (not shown)) in order to provide access to the interior of main housing 69. Top surface 88 includes a circular central recess 96 having a bottom surface 98. A first circular receiving orifice 100 extending through housing lid member 80 is provided at the center of central recess 96. Fingers 102 surrounding orifice 100 are provided on bottom surface 90. In addition, a second, uniquely shaped receiving orifice 104 (see description below) extending through housing lid member 80 is provided at the outer edge of central recess 96. A channel 106 is provided on bottom surface 90, and extends from orifice 104 to a post member 108.

Figure 6:
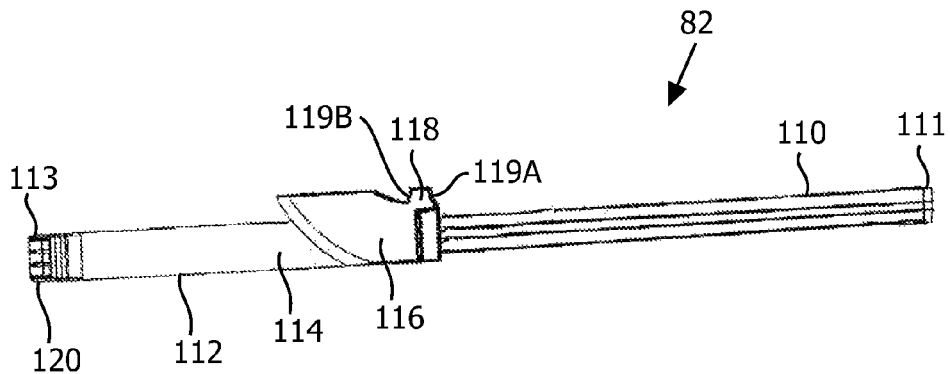
FIGS. 6 and 7 are top and bottom plan views, respectively, of a wire assembly forming a part of the connection assembly of FIGS. 2 and 3.
Figure 7:
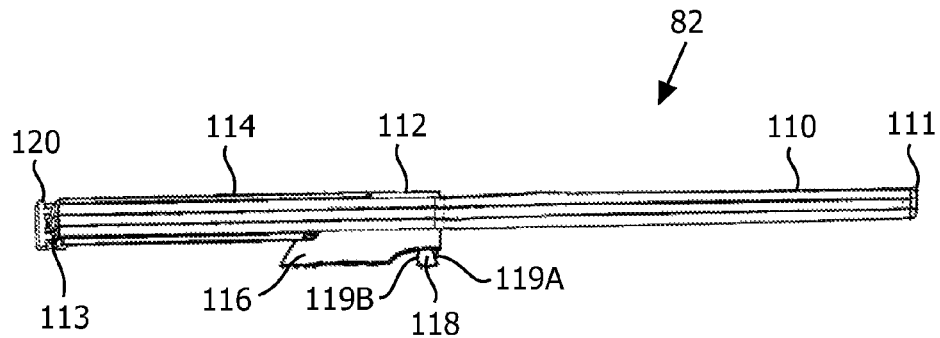
Figure 8:
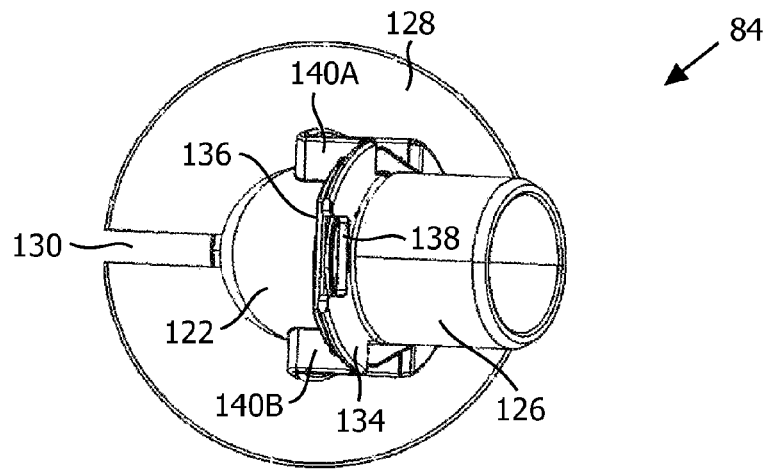
FIGS. 8, 9, 10, 11 and 12 are top plan, bottom plan, rear isometric, side elevational and rear elevational views, respectively, of a swivel connector member forming a part of the connection assembly of FIGS. 2 and 3.
Figure 9:
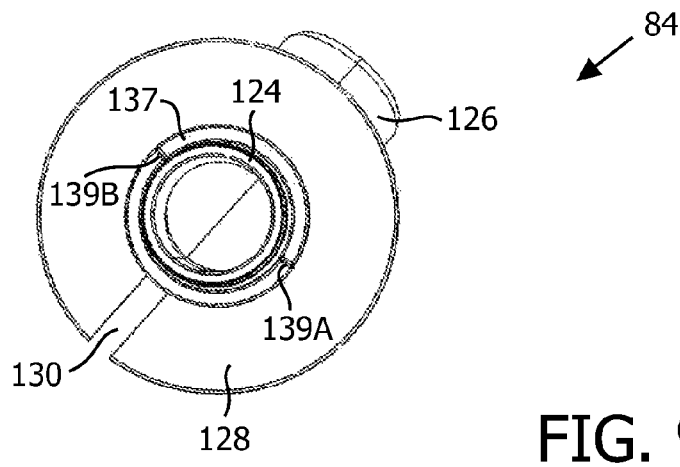
Figure 10:
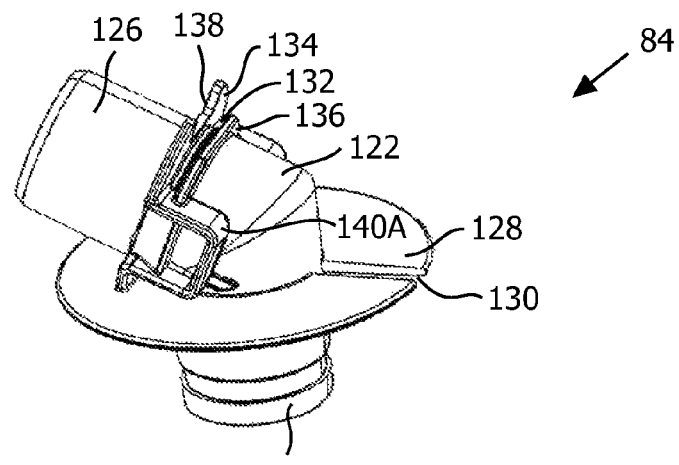
Figure 11:
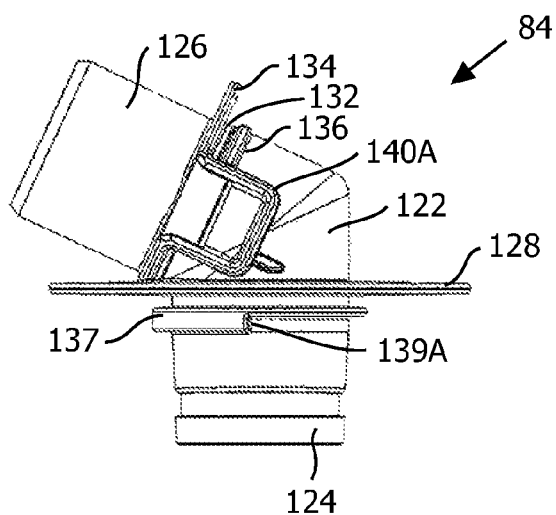
Figure 12:
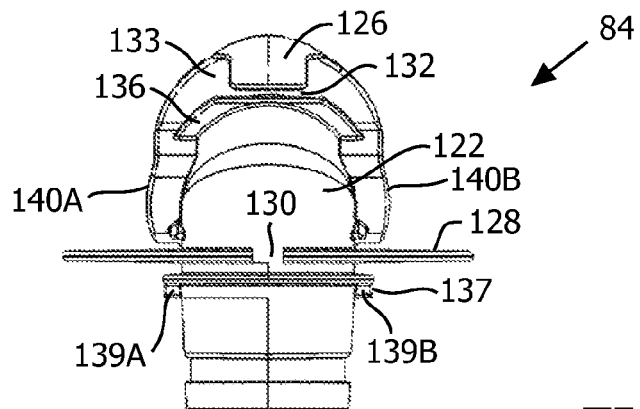

FIGS. 6 and 7 are top and bottom plan views, respectively, of wire assembly 82. In the exemplary embodiment, wire assembly 82 includes ribbon cable 110 that is received and held within wire management harness member 112. In alternative embodiments, other electrical wire members, such as one or more individual wires or a flex circuit, may be substituted for ribbon cable 110. Ribbon cable 110 includes a first end 111 and a second end 113. As seen in FIGS. 6 and 7, harness member 112 includes an elongated portion 114 and a generally arcuate portion 116 coupled to a first end of elongated portion 114. Generally arcuate portion 116 is sized and shaped to be received and held in receiving orifice 104 of housing lid member 80. When so received, the underside of arcuate portion 116 completes bottom surface 98 of central recess 96 (FIGS. 3 and 4). In addition, arcuate portion 116 includes a rotational limit feature 118. In the illustrated embodiment, rotational limit feature 118 comprises an engagement member having engagement surfaces 119A and 119B provided at the end of arcuate portion 116. An electrical connector 120 is provided at the end of elongated portion 114 opposite arcuate portion 116. The function of these elements is described below.

FIGS. 8, 9, 10, 11 and 12 are top plan, bottom plan, rear isometric, side elevational and rear elevational views, respectively, of swivel connector member 84. Swivel connector member 84 includes a conduit member 122 having a first end 124 structured to be coupled to the portion of delivery conduit 56 that is internal to main housing 69 and a second end 126 structured to be coupled to the portion of delivery conduit 56 that is external to main housing 69 (e.g., the heated tube). In the exemplary embodiment, conduit member 122 is in the form of an elbow conduit, although other shapes are also possible. Swivel connector member 84 also includes a circular base member 128 through which conduit member 122 extends. A slot 130 is provided in circular base member 128. The top end of conduit member 122 includes a channel 132 formed by walls 134 and 136, wherein wall 134 includes a cutout 138. Also, the sides of conduit member 122 each include a projecting wall member 140A, 140B attached to wall 134. Furthermore, a semicircular wall 137 having first and second end engagement surfaces 139A, 139B is provided on first end 124 below and adjacent to base member 128. The function of these components is described below.

Figure 13:
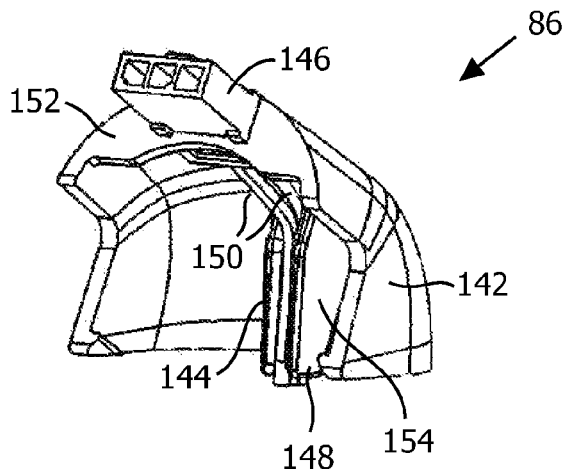
FIGS. 13, 14 and 15 are front isometric, rear isometric and bottom plan views, respectively, of a swivel cover assembly forming a part of the connection assembly of FIGS. 2 and 3.
Figure 14:
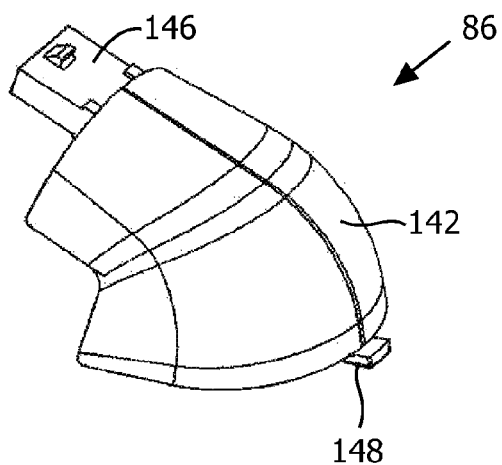
Figure 15:
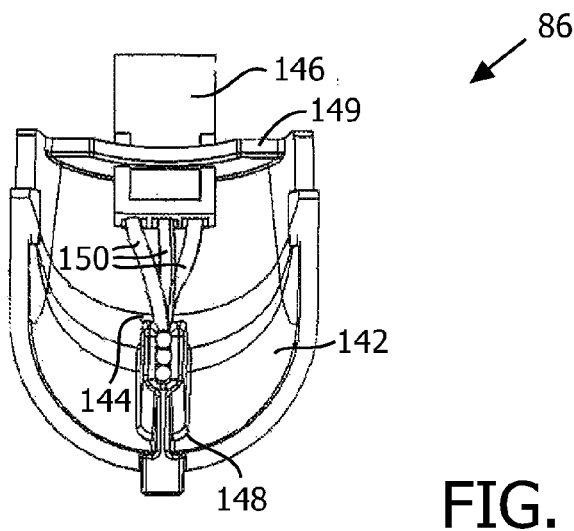

FIGS. 13, 14 and 15 are front isometric, rear isometric and bottom plan views, respectively, of swivel cover assembly 86. Swivel cover assembly 86 includes a hood member 142 that houses and supports an internal connector assembly 144. Connector assembly 144 includes a first electrical connector end 146 and a second electrical connector end 148 joined by wires 150. Hood member 142 also includes internal flange 152 at the top end thereof and recesses 154 provided on either side thereof.

Figure 16:
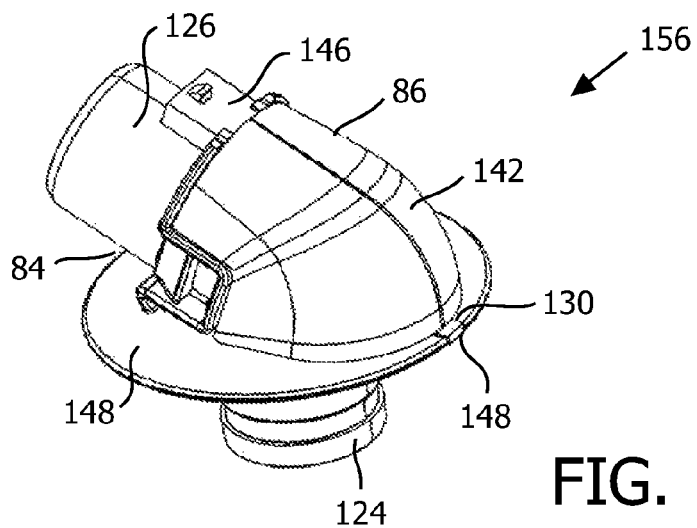
FIGS. 16 and 17 are rear isometric and bottom plan views, respectively, of a swivel assembly forming a part of the connection assembly of FIGS. 2 and 3.
Figure 17:
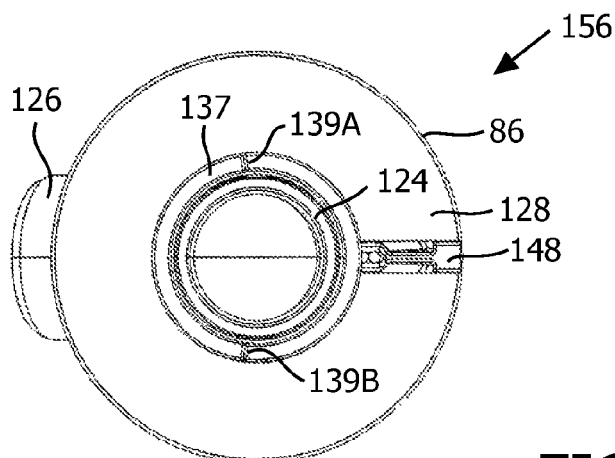

Assembly of connection assembly 78 begins by connecting swivel cover assembly 86 to swivel connector member 84 to form a swivel port assembly 156 as shown in FIGS. 16 and 17. In particular, swivel cover assembly 86 is coupled to swivel connector member 84 by inserting flange 152 into channel 132 and by inserting wall members 140A, 140B into respective recesses 154. In the exemplary embodiment, the two parts are secured to one another by a snap connection. In addition, as seen in FIG. 15, second electrical connector end 148 is positioned within slot 130.

Figure 18:
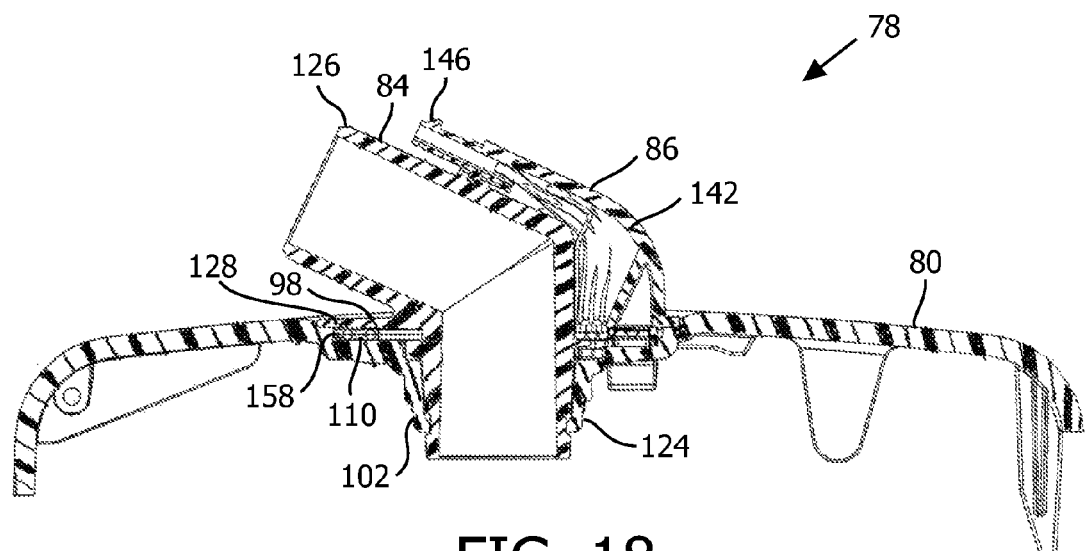
FIG. 18 is a cross-sectional view of the connection assembly of FIGS. 2 and 3.

Next, first end 111 of ribbon cable 110 of wire assembly 82 is physically and electrically coupled to second electrical connector end 148. Then, the portion of wire assembly 82 that includes harness member 112 is inserted through orifice 104 and first end 124 of conduit member 122 is inserted through receiving orifice 100 where it is gripped and held by fingers 102. As shown in FIG. 18, which is a cross sectional view of connection assembly 78, when this is done, a chamber 158 (described in greater detail below) will be created between base member 128 of swivel connector member 84 and bottom surface 98 of central recess 96 in which the free, spooled end of ribbon cable 110 sits. Ribbon cable 110 is then, in the exemplary embodiment, spooled around first end 124 of conduit member 122 one full revolution in a clockwise direction by rotating swivel port assembly 156. Elongated portion 114 of harness member 112 is then inserted into channel 106 and arcuate portion 116 is snapped into orifice 104 as shown in FIG. 3 to secure wire assembly 82 in place in the bottom of housing lid member 80. Also, electrical connector 120 is coupled to post member 108 as seen in FIG. 3 by inserting post member 80 into a slot provided in electrical connector 120.

Electrical connector 120 is electrically connected to heating control unit 72 within main housing 69 using one or more wires. In addition, first electrical connector end 146 is connected to heating coil 74 so that it is able to be selectively powered to provide the appropriate degree of heating for delivery conduit 56 under the control of heating control unit 72.

Figure 19:
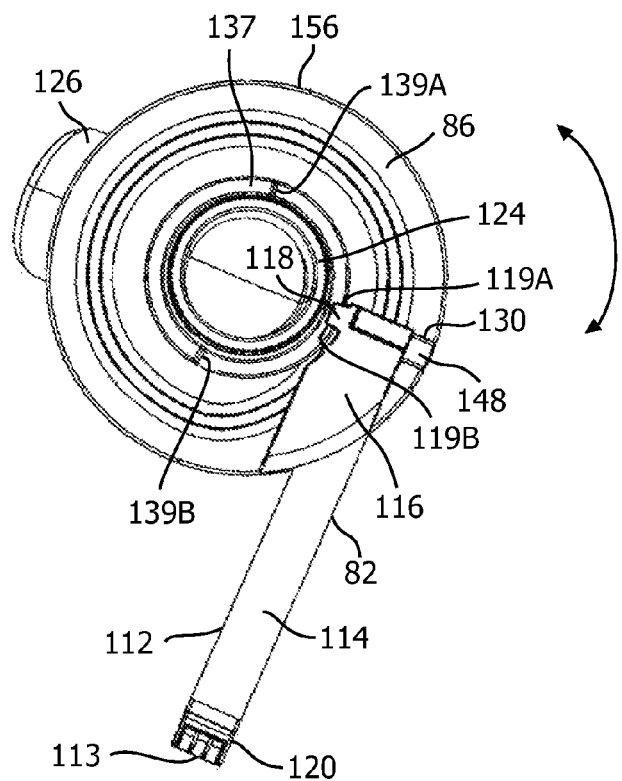
FIG. 19 is a schematic diagram showing a selected portion of the connection assembly of FIGS. 2 and 3.

When assembled in this manner, the orientation of swivel port assembly 156 relative to wire assembly 82 within connection assembly 78 is as shown in FIG. 19, wherein the other portions of connection assembly 78 have been omitted for illustration purposes. As seen in FIG. 19, the portion of arcuate portion 116 that includes rotational limit feature 118 is positioned adjacent to slot 130. As such, swivel port assembly 156 is able to rotate within central recess 96 of housing lid member as shown by the arrows in FIGS. 2 and 19. In addition, the degree of such rotation is limited by rotational limit feature 118. More specifically, swivel port assembly 156 is able to rotate in a first direction until such rotation is stopped by engagement surface 139A engaging engagement surface 119A, and in a second, opposite direction until such rotation is stopped by engagement surface 139B engaging engagement surface 119B. In the illustrated, non-limiting embodiment, this arrangement permits swivel port assembly 156 to rotate over about 180 degrees, although other rotational ranges less than 360 degrees are also possible (e.g., between about 20 degrees and about 270 degrees) depending on the position of engagement surfaces 139A and 139B (i.e, the arcuate length of semicircular wall 137).

When swivel port assembly 156 is rotated as just described, the free end of ribbon cable 110 sitting within chamber 158 will be caused to spool more and less tightly around first end 124 of conduit member 122 without allowing ribbon cable to pinch or tangle within chamber 158. In this manner, the radial size and height of chamber 158 is important and should be chosen so as to properly encase ribbon cable 110 and prevent such pinching and tangling from occurring (i.e., if chamber 158 is too large, ribbon cable may be able to pinch and tangle). In the exemplary embodiment, the height of chamber 158 is one to two times the diameter of the individual wire elements that are encased, with one and a half times being one particular implementation.

Thus, connection assembly 78 provides a simple and cost effective mechanism by which a heated tube may be electrically connected to pressure support system 50 in a manner that permits some degree of rotation of the heated tube relative to pressure support system 50. In addition, the mechanism of the present invention is not limited to use as a port for heated tubes, but instead may be used as a rotatable connection port for other types of accessory components that need to be electrically connected to pressure support system 50 in a rotating manner, such as, without limitation, a tube carrying an electrical wire coupled to a components, such as a sensor, attached to a mask. Also, use of connection assembly 78 is not limited to respiratory gas delivery systems, but instead may be used in other applications where it is necessary to rotatably and electrically connect an electrical accessory component to a main device or system.

It can be appreciated from the foregoing that the present invention provides a simple and cost effective outlet port for, for example, a respiratory therapy system that both provides power for a connected device, such as a heated tube, and allows for rotation of the connected device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A connection assembly for rotateably coupling an electrical accessory component to a main device and providing electrical power from the main device to the accessory component, comprising:
    a housing portion;
    a port assembly rotateably coupled to the housing portion, the port assembly having a first end and a second end configured to pass a gas therethrough, the second end of the port assembly being coupled to the accessory component, the port assembly including an electrical connector member having a first connector end electrically coupled to the accessory component and a second connector end; and
    a wire assembly having an electrical wire member having a first end electrically coupled to the second connector end and a second end electrically coupled to a power supply of the main device, wherein a portion of the electrical wire member is spooled around the first end of the port assembly and encased in a chamber defined between the housing portion and the port assembly, wherein the housing portion includes a recess having a bottom surface, wherein the port assembly is rotateably received within the recess, wherein the chamber extends from a bottom surface of a base portion of the port assembly to the bottom surface of the recess in a direction perpendicular to the bottom surface of the recess, wherein the chamber is sized to prevent the portion of the electrical wire member from pinching or tangling during rotation of the port assembly, wherein the electrical wire member includes at least one wire having a wire diameter, and wherein a height of the chamber measured in the direction is between one and two times the wire diameter, and wherein rotation of the port assembly in a first direction causes the portion of the electrical wire member to spool more tightly around the first end of the port assembly and rotation of the port assembly in a second direction causes the portion of the electrical wire member to spool less tightly around the first end of the port assembly.

2. The connection assembly according to claim 1, wherein the height of the chamber is one and a half times the wire diameter.

3. The connection assembly according to claim 1, wherein the wire assembly further includes a harness member, wherein a second portion of the electrical wire member separate from the spooled portion of the electrical wire member is received in an elongated portion of the harness member, and wherein the harness member is coupled to an inner surface of the housing portion adjacent to the recess.

4. The connection assembly according to claim 3, wherein the elongated portion is received in a channel provided on the inner surface of the housing portion.

5. The connection assembly according to claim 3, wherein the harness member includes a limit portion coupled to the elongated portion, wherein the limit portion is received in an orifice provided in the bottom surface of the recess, and wherein the limit portion is structured to limit rotation of the port assembly to less than 360 degrees.

6. The connection assembly according to claim 5, wherein the limit portion is structured to limit rotation of the port assembly to about 180 degrees.

7. The connection assembly according to claim 5, wherein the limit portion includes a limit feature having first and second engagement surfaces, wherein the port assembly includes a semicircular wall having third and fourth engagement surfaces, wherein the first engagement surface is structured to intermittently engage the third engagement surface and the second engagement surface is structured to intermittently engage the fourth engagement surface to limit rotation of the port assembly to less than 360 degrees.

8. The connection assembly according to claim 1, wherein the wire assembly is structured to limit rotation of the port assembly relative to the housing portion to less than 360 degrees.

9. The connection assembly according to claim 8, wherein the wire assembly includes a limit portion received in an orifice provided in the bottom surface of the recess, and wherein the limit portion is structured to limit rotation of the port assembly to less than 360 degrees.

10. The connection assembly according to claim 9, wherein the limit portion is structured to limit rotation of the port assembly to about 180 degrees.

11. The connection assembly according to claim 9, wherein the limit portion includes a limit feature having first and second engagement surfaces, wherein the port assembly includes a semicircular wall having third and fourth engagement surfaces, wherein the first engagement surface is structured to intermittently engage the third engagement surface and the second engagement surface is structured to intermittently engage the fourth engagement surface to limit rotation of the port assembly to less than 360 degrees.

12. A respiratory gas delivery system having a connection assembly according to claim 1, wherein the respiratory gas delivery system includes the accessory component of claim 1, wherein the connection assembly is coupled to the accessory component and is structured to provide electrical power to the accessory component, wherein the respiratory gas delivery system includes the main device of claim 1 and wherein the main device has a main housing coupled to the housing portion of the connection assembly.

13. The respiratory gas delivery system according to claim 12, wherein the accessory component is a heated gas delivery tube, wherein the port assembly includes a conduit member, wherein the second end of the conduit member is fluidly coupled to the heated gas delivery tube, and wherein the first end of the conduit member receives a flow of breathing gas generated by the respiratory gas delivery system.

14. The respiratory gas delivery system according to claim 13, wherein the port assembly further includes a cover member coupled to conduit, and wherein the electrical connector member is part of the cover member.

\* \* \* \* \*